United States Patent [19]

Marshall

[11] Patent Number: 5,379,703
[45] Date of Patent: Jan. 10, 1995

[54] MAYO STAND COVER FACILITATING STERILE DRAPING

[75] Inventor: Lyman R. Marshall, Asheville, N.C.

[73] Assignee: Scherer Healthcare Ltd., Asheville, N.C.

[21] Appl. No.: 185,688

[22] Filed: Jan. 24, 1994

[51] Int. Cl.6 .............................................. B65D 65/02
[52] U.S. Cl. ........................................ 108/90; 150/158
[58] Field of Search ............................ 108/90; 150/158

[56] References Cited

U.S. PATENT DOCUMENTS

| | | | |
|---|---|---|---|
| 3,044,517 | 7/1962 | Levi | 150/158 |
| 3,335,719 | 8/1967 | Boucher . | |
| 3,506,049 | 10/1967 | Gerald | 150/158 |
| 3,540,441 | 11/1970 | Collins . | |
| 3,738,405 | 6/1973 | Ericson | 108/90 |
| 3,747,655 | 7/1973 | Hadtke | 108/90 |
| 3,998,221 | 12/1976 | Collins | 108/90 |
| 4,750,402 | 6/1988 | Markey | 108/90 |

*Primary Examiner*—Kenneth J. Dorner
*Assistant Examiner*—Janet M. Wilkens
*Attorney, Agent, or Firm*—Carter & Schnedler

[57] ABSTRACT

A folded cover which may readily be transported and placed over the tray of a Mayo stand with little likelihood of becoming prematurely unfolded and being contaminated by contact with a non-sterile surface. The Mayo stand cover includes an elongated flat bag of sterilizable sheet material having an open bottom end and a closed top end, and sized to fit over the tray and a portion of the vertical support of the Mayo stand when unfolded. A cuff is formed over a portion of the bag at the open end. Sterile, gloved hands may be placed into the cuff for transporting the cover and slipping the cover over the Mayo stand. The remaining portion of the bag is folded so as to define a folded material portion adjacent to and outside the cuff. An element is provided for retaining the folded material portion in position prior to use of the bag as a cover and for releasing the folded material portion during use of the bag as a cover. In one form, the retaining element is a retaining tape arranged for retaining the folded material portion in position, and the retaining tape has an intermediate tearable portion for releasing the folded material portion. In another form, the retaining element is an adhesive pattern or double-sided adhesive tape.

18 Claims, 5 Drawing Sheets

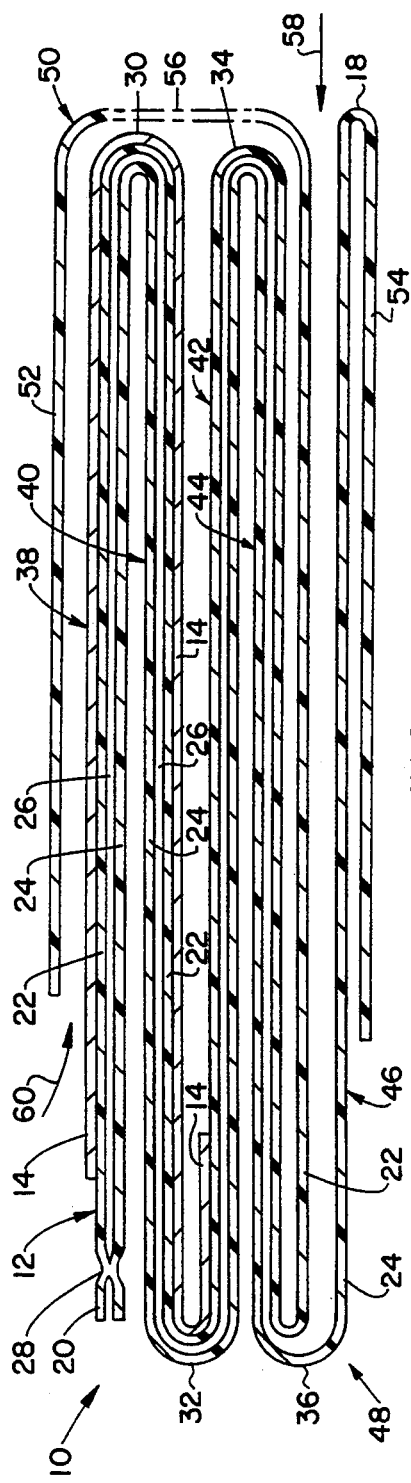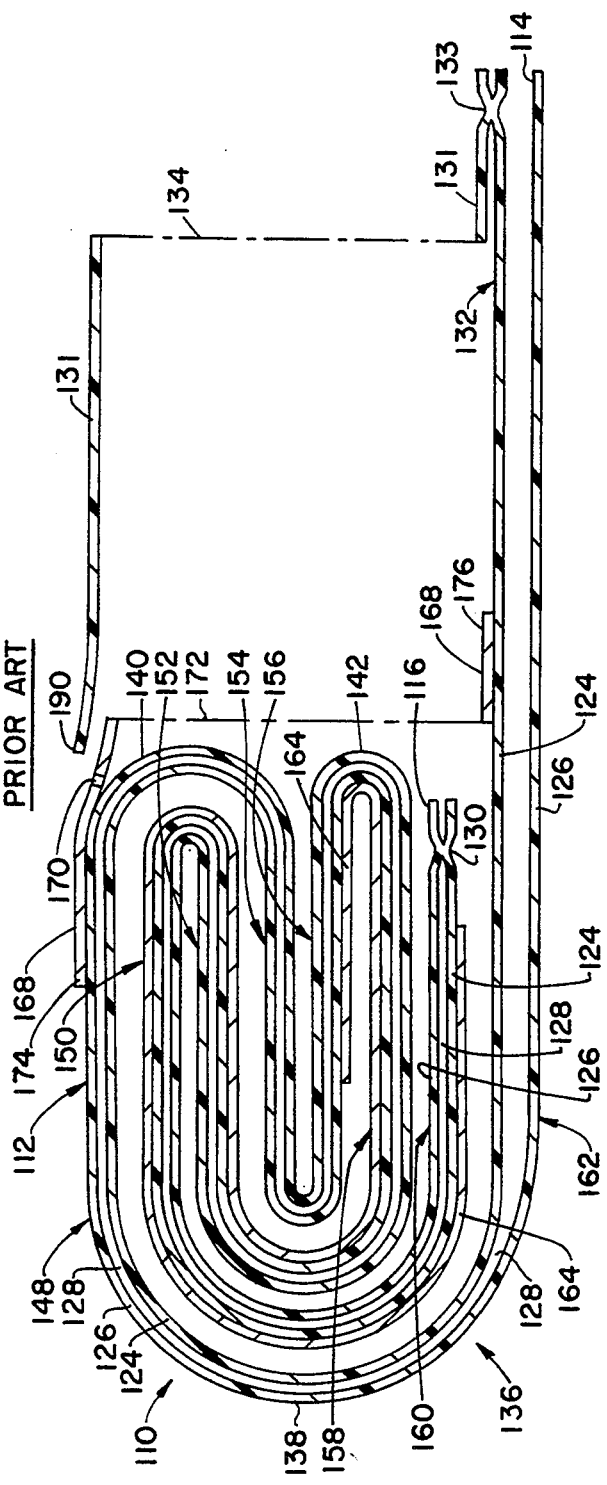
FIG. 2 PRIOR ART
FIG. 4

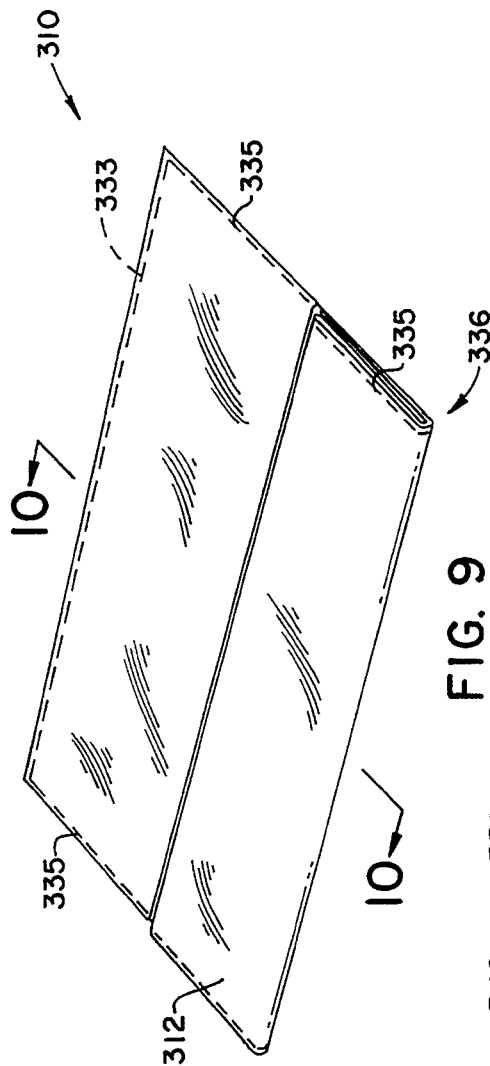
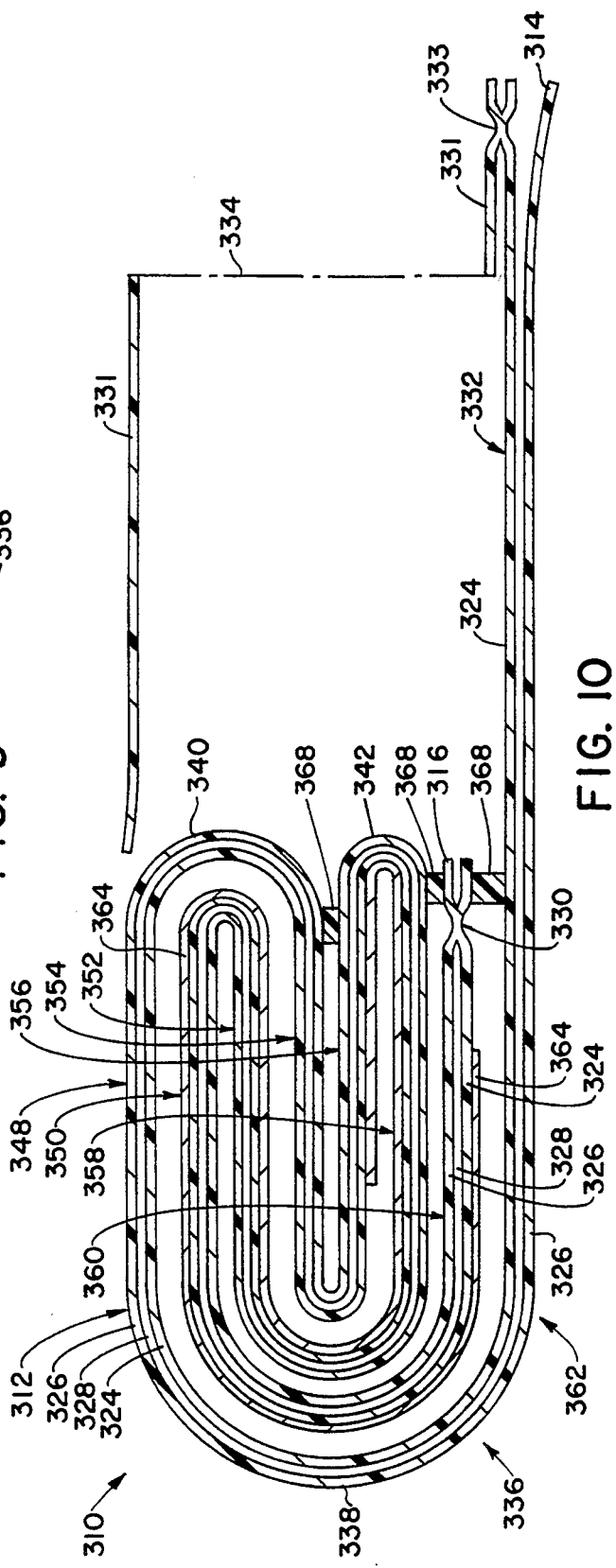
FIG. 9
FIG. 10

MAYO STAND COVER FACILITATING STERILE DRAPING

BACKGROUND OF THE INVENTION

The present invention relates generally to sterile, disposable Mayo stand covers and, more particularly, to a cover having features which facilitate draping over a Mayo stand without inadvertent loss of sterility through undesired contact of portions of the cover with non-sterile surfaces such as floor surfaces.

An item commonly employed in operating rooms is known as a Mayo stand, which is essentially a horizontal tray on a vertical support on which various instruments for surgical procedures are placed. In order to provide a sterile field with the least possible exposure of non-sterile parts of the stand, it is usual to employ a Mayo stand cover, which takes the general form of an elongated flat bag of sterilizable polyethylene tube material. The bag has an open bottom end and a closed top end and is placed over the tray and a major portion of the vertical support. A typical bag material is polyethylene film, and a thin pad of non-woven, cellulosic material, also sterile, is typically attached to the Mayo stand cover on the portion thereof directly over the tray in the in-use position.

Mayo stand covers are supplied by a manufacturer in a sterile condition within a sealed sterile package. The packaged Mayo stand cover is folded in a manner which facilitates handling and ready unfolding as the cover is installed over the Mayo stand. The Mayo stand cover is handled by a gloved, sterile nurse who at least begins the process by transporting the cover to the Mayo stand to begin slipping the cover over the Mayo stand, open end first.

In one known configuration, in its folded form a portion of the bag at the open end is turned back so as to define a cuff. Remaining portions of the bag are folded along transverse fold lines so as to define a folded material portion, which is tucked into the cuff and there retained during the initial steps of transporting the Mayo stand cover to the Mayo stand and beginning the installation process.

More particularly, during use, such a folded Mayo stand cover is transported by a nurse placing gloved hands inside the cuff, and then slipping the cuffed open end of the bag over the Mayo stand tray. By placing gloved, sterile hands within the cuff the nurse is able to slip the open end of the bag over the tray portion of the Mayo stand without danger of directly contacting the Mayo stand tray, which is considered non-sterile, and with no portion of the cover, other than the bag interior, coming into contact with any portion of the Mayo stand. Pushing from inside the cuff begins the process of moving the cuffed open end of the bag down the vertical support, as the bag material unfolds.

After the cover is placed over the tray portion of the Mayo stand and the cuffed open end pushed down the vertical support to begin the unfolding process, installation is completed by pulling the cuffed open end down over the vertical support, unfolding the Mayo stand cover so that it assumes the general configuration of an elongated flat bag.

The cuff thus serves dual purposes. One purpose is to facilitate transport and initial unfolding of the cover while preventing contact of the nurse's sterile, gloved hands with any portion of the Mayo stand. The other purpose is to provide a convenient way to retain the folded material portion during transport.

While generally effective, there are two disadvantages in particular of such prior art Mayo stand covers.

One disadvantage relates to the use of the Mayo stand cover and, in particular, the efficient transporting of the Mayo stand cover to the Mayo stand and the commencement of the unfolding process. While being transported by the gloved hands of the nurse being placed within the cuff, there is a tendency for the folded material to prematurely fall out of the cuff and onto the floor, or into contact with some other non-sterile surface. When this occurs, the Mayo stand cover is no longer suitable for use, and must be discarded.

Another disadvantage of such Mayo stand covers relates to efficient manufacturing. In particular, folding the bag and tucking it under the cuff is a labor-intensive operation, not particularly amenable to being accomplished by machine.

OBJECTS OF THE INVENTION

Accordingly, it is an object of the invention to provide a folded Mayo stand cover which may readily be transported and placed over the tray of a Mayo stand with little likelihood of becoming prematurely unfolded and being contaminated by contact with a non-sterile surface.

It is another object of the invention to provide a folded Mayo stand cover which is amenable to machine folding so as to minimize the labor involved in manufacture.

SUMMARY OF THE INVENTION

Briefly, and in accordance with the invention, a folded Mayo stand cover takes the form of an elongated flat bag of sterilizable non-woven sheet material having an open bottom end and a closed top end. The bag is sized to fit over the tray and a portion of the vertical support of the Mayo stand when unfolded. A cuff is formed over a portion of the bag at the open end, and a remaining portion of the bag is folded along transverse fold lines so as to define a folded material portion. The cuff may comprise a separate piece of material adhered to the portion of the bag at the open end. The folded material portion is adjacent to and outside of the cuff.

The folded cover additionally includes an element arranged for retaining the folded material portion in position prior to use of the bag as a cover, and for releasing the folded material portion during use of the bag as a cover. This retaining element alternately may comprise a pattern of tacky adhesive, double-sided adhesive tape, or a retaining tape arranged for retaining the folded material portion in position. In the event a retaining tape is employed, the retaining tape has an intermediate tearable portion for releasing the folded material portion.

Use of the Mayo stand cover of the invention in general commences as described hereinabove under the heading "Background of the Invention" in that a nurse with sterile, gloved hands placed inside the cuff transports the cover to the Mayo stand, and slips the cuffed open end over the tray portion of the Mayo stand, all without directly touching any part of the Mayo stand. While the cover is being transported by gloved hands placed within the cuff, the retaining tape or other retaining element positively prevents inadvertent unfolding of the folded portion of the cover. Once the cover is placed in its initial position over the tray portion of the Mayo stand, the folded material portion is released. In the case of a retaining element which comprises a retaining tape, the intermediate tearable portion of the retaining tape is torn. The installation process then continues generally as in the case of the prior art Mayo stand cover.

Since manufacture of the cover of the invention does not require that the folded material portion be tucked within the cuff, a hand folding operation, or at least a hand tucking operation, is avoided. Thus, the folded material portion is amenable to machine folding.

In a more particular embodiment of the invention, the retaining tape has end portions adhered to respective portions of the bag. Preferably, the intermediate tearable portion is free of adhesive, so that a gloved finger may readily be inserted under the tape so the tape may be pulled up and torn. In a more particular form, the intermediate tearable portion includes a perforated tear line, and a portion of the retaining tape immediately adjacent one side of the perforated tear line is free of adhesive. It is under this one side that a gloved finger is inserted for the tearing operation.

In a preferred configuration, one end portion of the retaining tape is adhered to the folded material portion, and another end portion of the retaining tape is adhered to a portion of the bag underlying the cuff. In this configuration, the nurse's hands can be placed within the cuff without exerting a tearing force on the tearable portion.

In another configuration, one end portion of the retaining tape is adhered to the folded material portion, and another end portion is adhered to the cuff, such as to the top of the cuff.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 2 is a section, greatly exaggerated in thickness, taken on line 2—2 of FIG. 1;

FIG. 4 is a section, greatly exaggerated in thickness, taken along line 4—4 of FIG. 3;

FIG. 9 is a three dimensional view of a folded Mayo stand cover in accordance with a third embodiment of the invention; and FIG. 10 is a section, greatly exaggerated in thickness, taken along line 10—10 of FIG. 9.

DETAILED DESCRIPTION OF THE PREFERRED EMBODIMENTS

Figure 1:
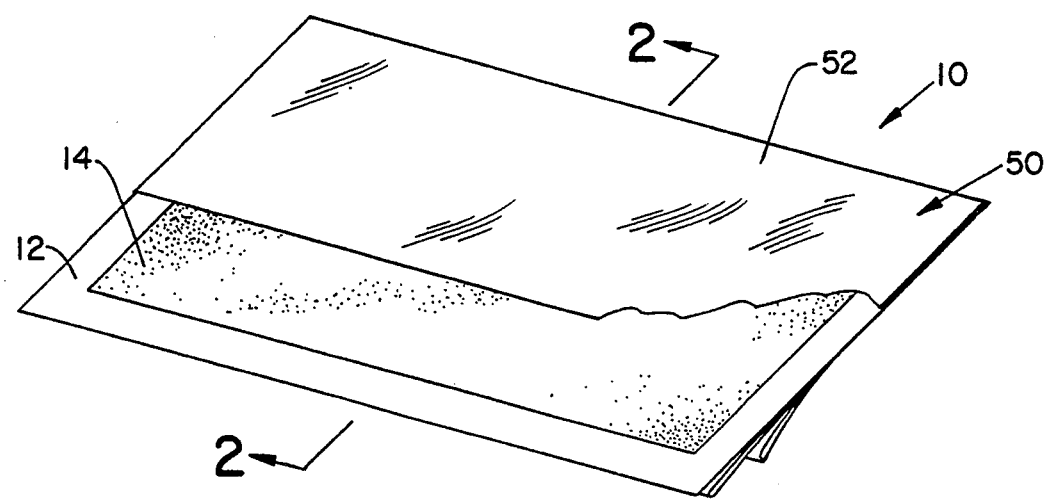
FIG. 1 is a three dimensional view of a prior art folded Mayo stand cover, partly broken away.

Referring initially to FIGS. 1 and 2, a prior art Mayo stand cover 10 comprises an elongated flat bag 12 of sterilizable sheet material, such as polyethylene. The cover 10 includes a thin sheet of cellulosic material 14 positioned and glued on the bag 12 so as to be over the tray portion of a Mayo stand when installed. Although folded in FIGS. 1 and 2, it will be appreciated that the bag 12 when folded has an open bottom end 18 and a closed top end 20, and is sized to fit over the tray and a portion of the vertical support member of a Mayo stand.

The bag 12 more particularly has an upper polyethylene film layer 22 and a lower polyethylene film layer 24 which, for purposes of illustration, are separated by a space 26. (The terms "upper" and "lower" are with reference to the relative orientations of the layers 22 and 24 when unfolded.) However, particularly when folded as in FIGS. 1 and 2, it will be appreciated that the upper and lower film layers 22 and 24 generally are in contact, and in many places the space 26 does not exist. The closed end 20 is defined by the layers 22 and 24 being heat sealed at 28. In this prior art configuration, the body of the bag 12 is formed of flattened polyethylene tube material, appropriately cut to length consistent with the heat seal 28.

Most of the bag 12 is folded along transverse fold lines 30, 32, 34 and 36 to form folded sections 38, 40, 42, 44 and 46, which together define a folded material portion, generally designated 48. Each of the folded sections 38, 40, 42, 44 and 46 includes corresponding portions of the upper and lower film layers 22 and 24. In addition, portions of the sheet of cellulosic material 14 are included in the folded sections 38 and 40, and a portion is included in the folded material section 42.

A portion of the prior art bag 12 at the open end 18 is turned back so as to define a cuff generally designated 50, and more particularly having upper and lower cuff portions 52 and 54. The folded material portion 48 is tucked inside the cuff 50 and, more particularly, between the upper cuff portion 52 and the upper film layer 22 of the folded section 46 near the open end 18. The lower cuff portion 54 is directly adjacent the lower film layer 24 of the folded section 46.

It will be appreciated that, for purposes of illustration, the thicknesses of the layers in FIG. 2 are greatly exaggerated. Moreover, to avoid undue distortion, a phantom line is employed at 56 to represent a portion of the fold defining the upper cuff portion 52, which fold portion otherwise would be distorted through elongation in FIG. 2.

In FIG. 2, an arrow 58 represents relative movement of the tray portion of the Mayo stand into the open end 18 of the bag 12 being placed over the Mayo stand, and an arrow 60 designates the point where a nurse's hand is placed under the upper cuff portion 52 for transporting the cover 10.

The prior art Mayo stand cover 10 is used as described hereinabove under the heading "Background of the Invention". As noted hereinabove, the folded material portion 48, while generally retained within the cuff 50, and in particular under the upper portion 52 of the cuff 50, nevertheless is susceptible to falling out, especially when a nurse's hands are under the upper portion 52 of the cuff 50 for carrying.

Figure 5:
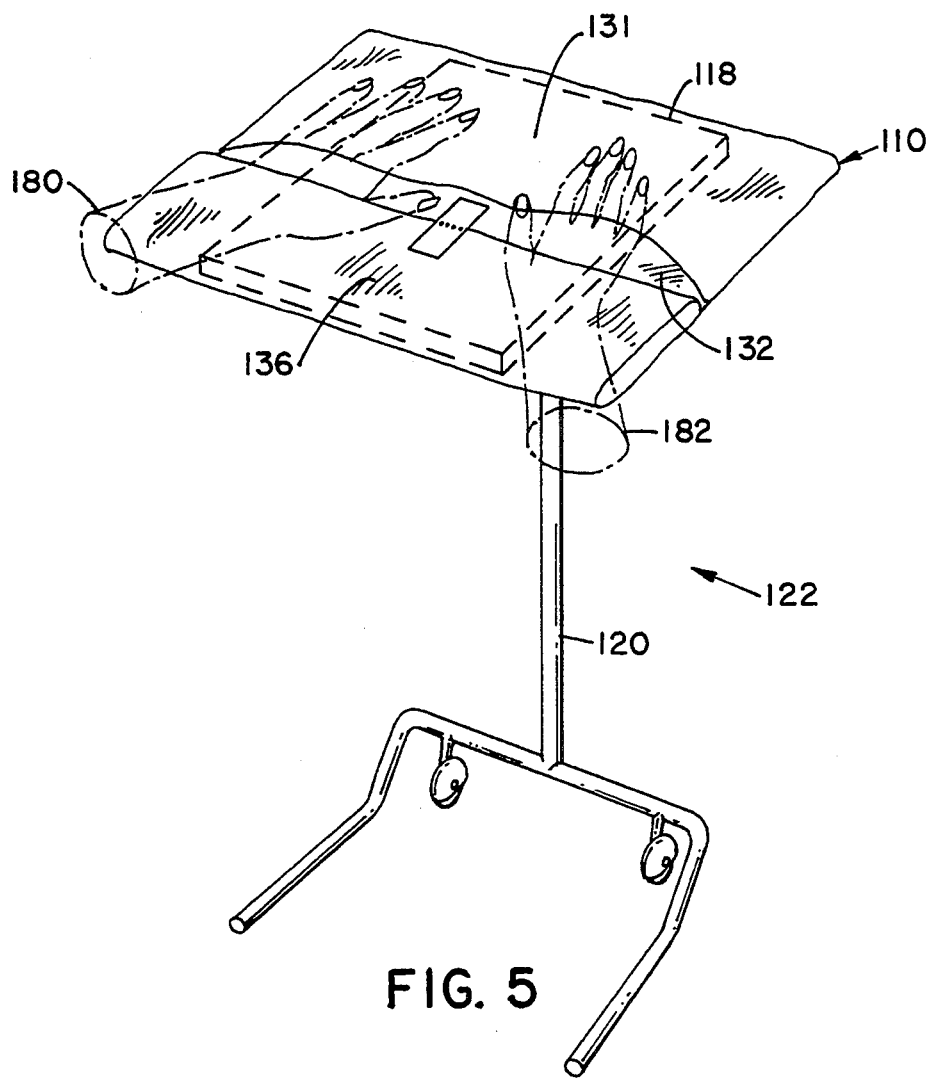
FIG. 5 is a three dimensional view of the Mayo stand cover of FIGS. 3 and 4 being placed initially in position over the tray portion of a Mayo stand.

With reference now to FIGS. 3, 4, 5 and 6, a Mayo stand cover 110 in accordance with a first embodiment of the invention likewise comprises an elongated flat bag 112 of sterilizable sheet material, such as polyethylene. The bag 112, when unfolded, has an open bottom end 114 and a closed top end 116, and fits over the tray 118 and vertical support 120 portions of a Mayo stand 122 (FIG. 5). FIG. 4, like FIG. 2, for purposes of illustration is greatly exaggerated in thickness.

The bag 112 more particularly includes an upper polyethylene film layer 124 and a lower polyethylene film layer 126 which, for purposes of illustration, are separated by a space 128. (Again, the terms "upper" and "lower" are with reference to the relative orientations of the layers 124 and 126 when unfolded.) However, particularly when folded as in FIGS. 3 and 4, it will be appreciated that the upper and lower film layers 124 and 126 generally are in contact, and in many places the space 128 does not exist. The closed end 116 is defined by the layers 124 and 126 being heat sealed at 130.

At the open bottom end 114, a cuff 131 is formed over a portion 132 of the bag 112. Unlike the cuff 50 of the prior art bag 12 of FIGS. 1 and 2 formed by turning back a portion of the bag, the cuff 131 of the cover 110 of FIGS. 3-5 preferably comprises a separate piece of material adhered to the bag portion 132 such as by heat sealing indicated at 133. (To avoid distortion in view of the exaggerated thickness of FIG. 4, the cuff 131 is broken into upper and lower portions by a phantom line 134; thus the upper and lower portions of the cuff 131 are actually continuous, as the cuff 131 is broken merely for purposes of illustration.)

This construction facilitates less expensive manufacture, as the upper polyethylene film layer 124, the lower polyethylene film layer 126 and the cuff 131 initially comprise separate pieces which are heat sealed together to form a bag configuration. This is in contrast to the prior art construction where the body of the bag 12 (FIGS. 1 and 2) is formed of flattened polyethylene tube material. Thus, in FIG. 3, heat seals between the layers 124 and 126 running along the sides of the bag 112 are represented as dash lines 135. During manufacture, bags 112, prior to folding and in the form of separate pieces comprising the layers 124 and 126 and the cuff 131, preferably move in a direction perpendicular to the length of the bag 112 along a heat sealing machine (not shown) which forms the various heat seals 130, 133 and 135. This is in contrast to the manufacturing process for the prior art bags 12, which typically move lengthwise along the heat sealing machine for forming the heat seal 28. An increased rate of production is thus facilitated by the configuration of the invention.

In addition, the cuff 131, being formed of a separate piece of material, advantageously may have a different color from the rest of the bag 112 in order to draw attention to the cuff 131. An appropriate legend may be printed on the cuff 131, such as "place hands under cuff".

The remaining portion of the bag 112 comprises a folded material portion, generally designated 136, and is folded along transverse fold lines 138, 140 and 142 as depicted in FIG. 4 to form folded sections 148, 150, 152, 154, 156, 158, 160 and 162. Each of the folded sections 148, 150, 152, 154, 156, 158, 160 and 162 includes corresponding portions of the upper and lower film layers 124 and 126. Significantly, the folded material portion 136 is adjacent to and outside of the cuff 131.

Also included is a sheet 164 of cellulosic material glued to the bag 112 in a position such that, when the bag 112 is completely unfolded, the sheet 164 overlies the bag 112 over the tray portion 118 of the Mayo stand 122, the sheet 164 beginning immediately adjacent the closed end 116. In the folded configuration, portions of the sheet of cellulosic material 164 are included in the folded sections 160, 150, 152 and 158, and a portion is included in the folded material section 156.

For retaining the folded material portion 136 in position, a piece of retaining tape 168 is provided, the retaining tape 168 having an intermediate tearable portion preferably comprising perforations 170. When torn, the intermediate tearable portion releases the folded material portion 136. A single retaining tape 168 is sufficient, positioned laterally in the center of the cover 110. (To avoid undue distortion in view of the exaggerated thickness in FIG. 4, the retaining tape 168 for purposes of illustration is broken on a phantom line 172; the tape 168 is actually a continuous piece.)

The tape 168 includes an end portion 174 adhered to the folded material portion 136, and another end portion 176 adhered to the portion 132 of the bag underlying the cuff 131 and, more particularly, to a portion of the upper film layer 124 underlying the cuff 131, such that a person's hands can be placed within the cuff 131 without exerting a tearing force on the tearable portion 170 of the tape 168. This feature is perhaps best seen in FIG. 5 wherein the cuff 131 is lifted up by a pair of hands 180 and 182. FIG. 5 thus depicts the Mayo stand 122 having the horizontally disposed tray 118 and a vertical support 120, with the folded cover 110 of the invention being placed in its initial position over the tray 118, and being manipulated by means of the hands 180 and 182 placed under the cuff 131.

Figure 6:
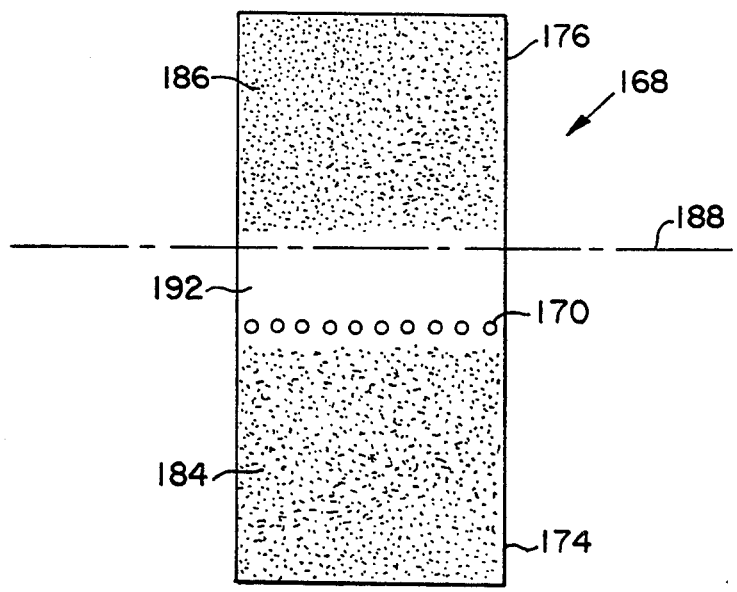
FIG. 6 is an enlarged view of the underside of the retaining tape included in the Mayo stand cover of FIGS. 3 and 4.

Considering the retaining tape 168 in greater detail, FIG. 6 depicts the underside of the tape 168 and, in particular, adhesive areas 184 and 186 on the undersides of the respective end portions 174 and 176. In FIG. 6, a phantom line 188 depicts the approximate position of the folded edge 140 (FIG. 4), there being a slight gap between the end 190 of the cuff 131 and the edge 140 when the cover 110 is in the folded position illustrated.

As may be seen in FIG. 6, immediately adjacent one side of the perforated tear line 170 is a region 192 which is free of adhesive. This adhesive-free region 192 provides an essentially loose area of the tearable retaining tape 168 under which a nurse's finger may readily be inserted to begin the tearing process, which otherwise would be more difficult. In addition, the adhesive-free region 192 obviates the need for precise positioning of the tear line 170 at the folded edge 140.

While a particular folding configuration is illustrated for the folded material portion 136, it will be appreciated that any suitable configuration may be employed. The illustrated configuration, however, advantageously is amenable to machine folding. In addition, it will be appreciated that a bag and cuff configuration generally like that of FIGS. 1 and 2 may be employed in combination with a retained folded material portion in accordance with the invention, that is, a bag formed of flattened tube material, with a cuff formed by folding back a portion of the bag 112 at the open bottom end 114.

Figure 7:
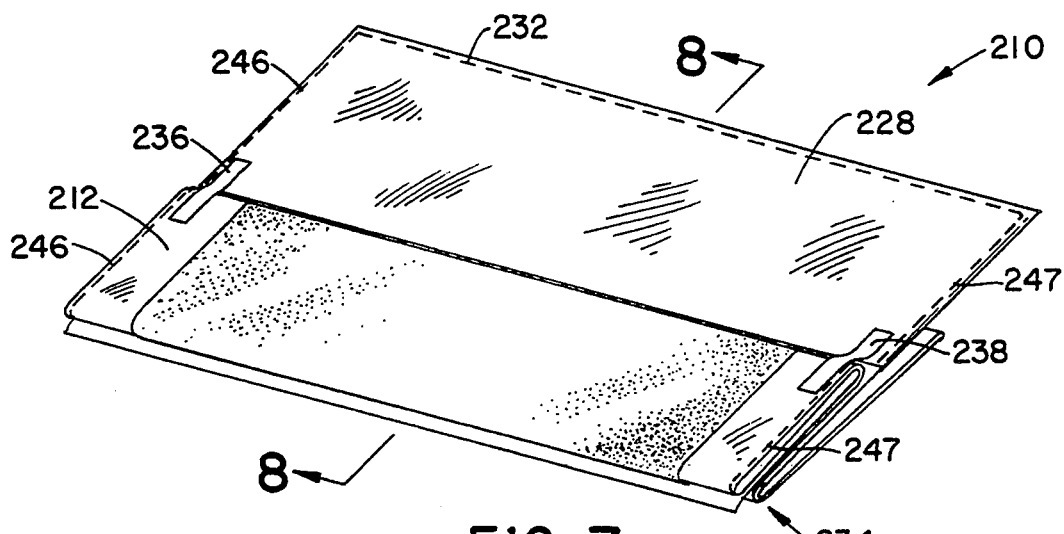
FIG. 7 is a three dimensional view of a folded Mayo stand cover in accordance with a second embodiment of the invention.
Figure 8:
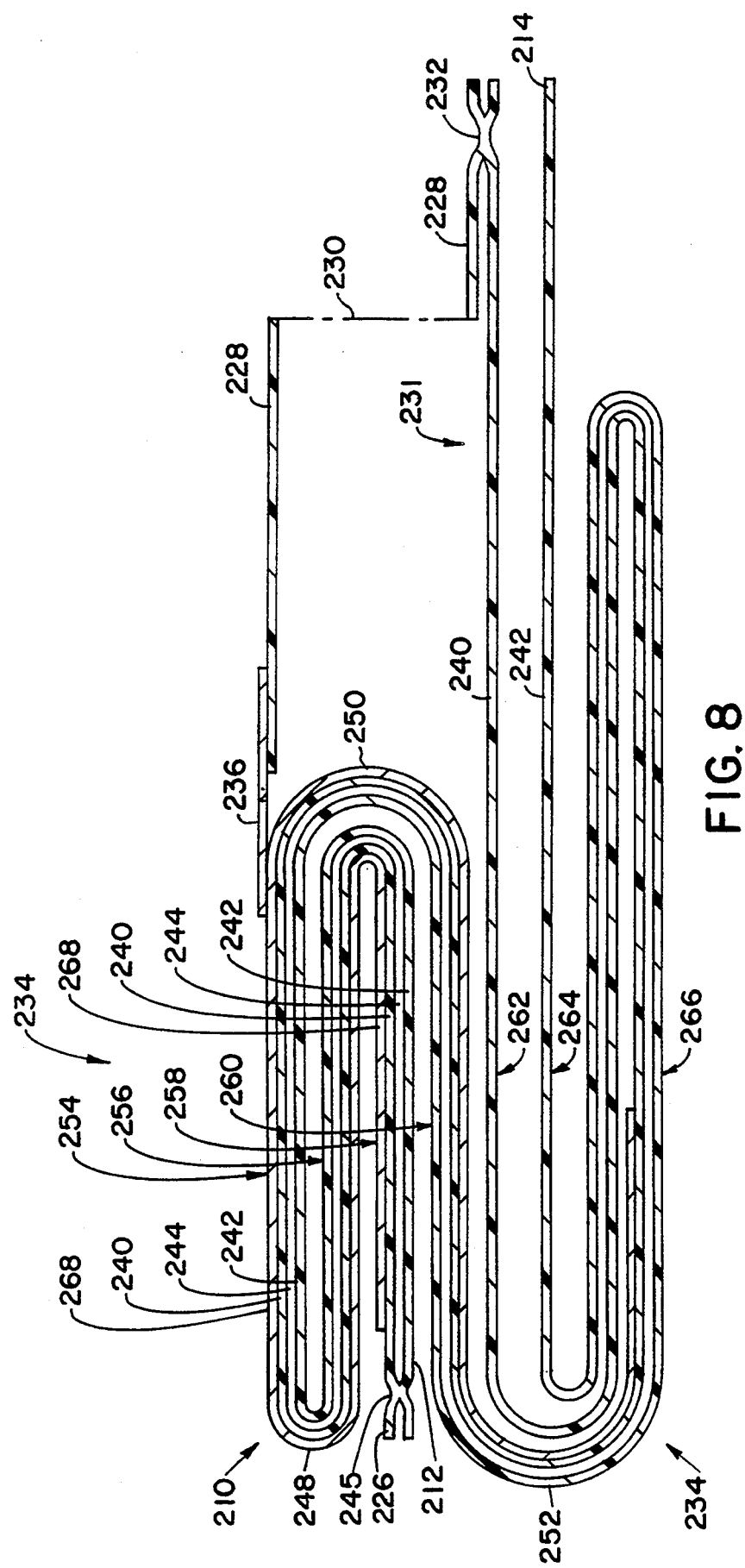
FIG. 8 is a section, greatly exaggerated in thickness, taken along line 8—8 of FIG. 7.

Referring next to FIGS. 7 and 8, depicted is a Mayo stand cover 210 in accordance with a second embodiment of the invention. As in the case of the cover 110, the cover 210 comprises an elongated flat bag 212 of sterilizable sheet material, such as polyethylene, which when unfolded, has an open bottom end 214 and a closed top end 226, and fits over the tray and vertical support portions of a Mayo stand. Formed over the open bottom end 214 of the bag 212 is a cuff 228. For purposes of illustration only to avoid undue distortion in view of the exaggerated vertical thickness in FIG. 8, the cuff 228 is broken into upper and lower portions connected by a phantom line 230. Preferably the cuff 228 comprises a separate piece of material joined to a portion 231 of the bag 212 by a heat seal indicated at 232. A folded material portion generally designated 234 is adjacent to and outside of the cuff 228.

The folded cover 210 of FIGS. 7 and 8 differs from the folded cover 110 of FIGS. 4 and 5 in that two pieces 236 and 238 of tearable retaining tape are employed, positioned near the sides of the cover 210, and the manner of tape attachment differs. One end portion of each of the retaining tapes 236 and 238 is adhered to the folded material portion 234, and another is adhered to the cuff 228 itself.

The bag 212 more particularly includes an upper polyethylene film layer 240 and a lower polyethylene film layer 242 which, for purposes of illustration, are separated by a space 244. The closed end 226 is defined by the layers 240 and 242 being heat sealed at 245. Represented in FIG. 7 as dash lines are heat seals 246 and 247 between the polyethylene film layers 240 and 242 running along the side of the bag 212.

The folded material portion 234 is folded along transverse fold lines 248, 250 and 252 as depicted in FIG. 8 to form folded sections 254, 256, 258, 260, 262, 264 and 266. Each of the folded sections 254, 256, 258, 260, 262, 264 and 266 includes corresponding portions of the upper and lower film layers 240 and 242.

Also included is a sheet 268 of cellulosic material glued in a position such that, when the bag 212 is completely unfolded, the sheet 268 overlies the tray portion of the Mayo stand. In the folded configuration, portions of the sheet of cellulosic material 268 are included in the folded sections 258, 256, 254 and 260, and a portion is included in the folded material section 266.

Figure 3:
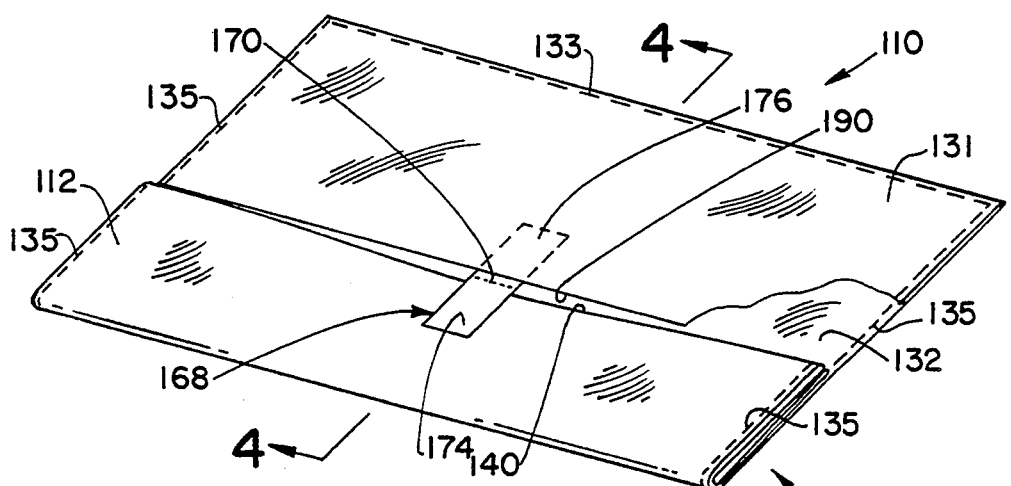
FIG. 3 is a three dimensional view, partly broken away, of a folded Mayo stand cover in accordance with a first embodiment of the invention.

While generally serving the purpose of retaining the folded material portion 234 in position, a disadvantage of the configuration of the cover 210 of FIGS. 7 and 8 compared to the cover 110 of FIGS. 3 and 4 is that there is more potential for inadvertent tearing of the pieces of retaining tape 236 and 238, due to their being positioned at the top of the cuff 228 and accordingly subject to tearing force merely by the insertion of hands under the cuff 228, even though this tearing force can be minimized by having the tearable pieces of retaining tape located near the edges.

Referring finally to FIGS. 9 and 10, depicted is a Mayo stand cover 310 in accordance with a third embodiment of the invention. In overall configuration, the cover 310 is similar to the cover 110 of FIGS. 3-6, and comprises an elongated flat bag 312 of sterilizable sheet material, such as polyethylene which, when unfolded, has an open bottom end 314 and a closed top end 316, and fits over the tray and vertical support portions of a Mayo stand.

The bag 312 more particularly includes an upper polyethylene film layer 324 and a lower polyethylene film layer 326 which, for purposes of illustration, are separated by a space 328. Particularly when folded as in FIGS. 9 and 10, it will be appreciated that the upper and lower film layers 324 and 326 generally are in contact, and in many places the space 328 does not exist. The closed end 316 is defined by the layers 324 and 326 being heat sealed at 330.

At the open bottom end 314, a cuff 331 is formed over a portion 332 of the bag 312, and preferably comprises a separate piece of material adhered to the bag portion 332 such as by heat sealing indicated at 333. For purposes of illustration to avoid undue distortion in view of the exaggerated vertical thickness in FIG. 10, the cuff 331 is broken into upper and lower portions connected by a phantom line 334; the cuff 331 is actually a continuous piece. Heat seals between the layers 324 and 326 running along the sides of the bag 312 are represented as dash lines 335 in FIG. 9.

The remaining portion of the bag 312 comprises a folded material portion, generally designated 336, and is folded along transverse fold lines 338, 340 and 342 as depicted in FIG. 10 to form folded sections 348, 350, 352, 354, 356, 358, 360 and 362. Each of the folded sections 348, 350, 352, 354, 356, 358, 360 and 362 includes corresponding portions of the upper and lower film layers 324 and 326 The folded material portion 336 is adjacent to and outside of the cuff 331.

A sheet 364 of cellulosic material is glued to the bag 312 in a position such that, when the bag 312 is completely unfolded, the sheet 364 overlies the bag 312 over the tray portion of a Mayo stand, the sheet 364 beginning immediately adjacent the closed end 316. In the folded configuration, portions of the sheet of cellulosic material 364 are included in the folded sections 360, 350, 352 and 358, and a portion is included in the folded material section 356.

The folded cover 310 of FIGS. 9 and 10 differs from the folded cover 110 of FIGS. 4 and 5 in that an alternative element is employed for retaining the folded material portion 336 in position prior to use of the bag 312 as a cover, and for releasing the folded material portion during use of the bag 312 as a cover. Thus, rather than the retaining tape 168 (FIGS. 3, 4 and 6) or the retaining tapes 236 and 238 (FIGS. 7 and 8), in FIG. 10 at least one adhesive element 368 is appropriately positioned among the folded sections 348, 350, 352, 354, 356, 358, 360 and 362 so as to retain the folded material portion 336 in position. In the particular configuration illustrated, three adhesive elements 368 are employed. However, it will be appreciated that the positioning of the adhesive elements 368 in FIG. 10 is exemplary only, and any positioning and combination of adhesive elements 368 may be employed which serves the intended purpose.

As one more particular example, the adhesive element 368 may comprise a pattern of adhesive such as a series of adhesive dots, an adhesive line, or a series of adhesive lines. As another example, the adhesive element may comprise double-sided tape. In the case of an adhesive pattern, a tacky hot melt adhesive may be employed. In the case of double-sided tape, a suitable tacky tape may be employed.

In view of the foregoing, it will be appreciated that the present invention provides a folded Mayo stand cover including a hand-receiving cuff facilitating transport, a folded bag portion outside of the cuff, and a suitable attachment element for retaining the folded portion in position prior to use of the bag as a cover and for releasing the folded portion during use of the bag as a cover. As a result, the cover may readily be transported and placed over the tray of a Mayo stand with little likelihood of becoming prematurely unfolded and being contaminated by contact with a non-sterile surface, and yet is readily unfoldable for use. In addition, manufacturing cost is reduced.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A folded cover for an instrument stand having a horizontally disposed tray and a vertical support therefor, said cover comprising:

an elongated flat bag of sheet material, said bag having an open bottom end and a closed top end and sized to fit over the tray and a portion of the vertical support when unfolded;

a cuff formed over a portion of said bag at said open end;

a remaining portion of said bag being folded along transverse fold lines so as to define a folded material portion, said folded material portion being adjacent to and outside of said cuff; and an element arranged for retaining said folded material portion in position prior to use of said bag as a cover and for releasing said folded material portion during use of said bag as a cover.

2. A folded cover in accordance with claim 1, wherein said folded material portion has a configuration amenable to machine folding.

3. A folded cover in accordance with claim 1, wherein said cuff comprises a separate piece of material adhered to said portion of said bag at said open end.

4. A folded cover in accordance with claim 3, wherein said separate piece of material has a different color than said bag.

5. A folded cover in accordance with claim 1, wherein said element comprises an adhesive pattern.

6. A folded cover in accordance with claim 1, wherein said element comprises double-sided adhesive tape.

7. A folded cover in accordance with claim 1, wherein said element comprises a retaining tape.

8. A folded cover in accordance with claim 7, wherein said retaining tape has an intermediate tearable portion.

9. A folded cover in accordance with claim 8, wherein said retaining tape has end portions adhered to respective portions of said bag and wherein said intermediate tearable portion is free of adhesive.

10. A folded cover in accordance with claim 9, wherein said intermediate tearable portion comprises a perforated tear line, and a portion of said retaining tape immediately adjacent one side of said perforated tear line is free of adhesive.

11. A folded cover in accordance with claim 8, wherein said retaining tape has one end portion adhered to said folded material portion and another end portion adhered to a portion of said bag underlying said cuff such that a person's hands can be placed within said cuff without exerting a tearing force on said tearable portion.

12. A folded cover in accordance with claim 11, wherein said intermediate tearable portion is free of adhesive.

13. A folded cover in accordance with claim 12, wherein said intermediate tearable portion comprises a perforated tear line, and a portion of said retaining tape immediately adjacent one side of said perforated tear line is free of adhesive.

14. A folded cover in accordance with claim 11, wherein said one end portion is adhered near an edge of said folded material portion adjacent said cuff.

15. A folded cover in accordance with claim 8, wherein said retaining tape has one end portion adhered to said folded material portion and another end portion adhered to said cuff.

16. A folded cover in accordance with claim 15, wherein said intermediate tearable portion is free of adhesive.

17. A folded cover in accordance with claim 16, wherein said intermediate tearable portion comprises a perforated tear line, and a portion of said retaining tape immediately adjacent one side of said perforated tear line is free of adhesive.

18. A folded cover in accordance with claim 15, wherein said one end portion is adhered near an edge of said folded material portion adjacent said cuff.

* * * * *